US 7,569,711 B2
Aug. 4, 2009

(12) United States Patent
Ganem et al.

(10) Patent No.: US 7,569,711 B2
(45) Date of Patent: Aug. 4, 2009

(54) ENONE CANCER THERAPEUTICS

(75) Inventors: Bruce Ganem, Ithaca, NY (US); Donald J. Creighton, Baltimore, MD (US); Diana S. Hamilton, Catonsville, MD (US); Zhebo Ding, Ithaca, NY (US)

(73) Assignee: Cornell Univeristy, Ithaca, NY (US)

( * ) Notice: Subject to any disclaimer, the term of this patent is extended or adjusted under 35 U.S.C. 154(b) by 0 days.

(21) Appl. No.: 11/006,132

(22) Filed: Dec. 7, 2004

(65) Prior Publication Data
US 2005/0233975 A1 Oct. 20, 2005

Related U.S. Application Data

(63) Continuation of application No. 10/098,834, filed on Mar. 15, 2002, now abandoned.

(51) Int. Cl.
C07C 59/147 (2006.01)
C07C 59/185 (2006.01)
C07C 315/00 (2006.01)
C07C 317/00 (2006.01)

(52) U.S. Cl. .......................... 554/118; 554/119; 568/37
(58) Field of Classification Search ................ 554/118, 554/119; 568/37
See application file for complete search history.

(56) References Cited

OTHER PUBLICATIONS

Aghil et al. (DN 116:227668, HCAPLUS, abstract of Anti Cancer Drug Design (1992), 7(1), 67-82).*
Izawa et al. (DN 106:49660, HCAPLUS, abstract of JP 61134340).*
Tsuji et al. (DN 108:111864, HCAPLUS, abstract of JP 62129235).*
Diana S. Hamilton, et al., "Glutathionyl Transferase Catalyzed Addition of Glutathione to COMC: A New Hypothesis for Antitumor Activity", *Organic Letters 2002*, vol. 4, No. 7, 1209-1212; published on Web Mar. 3, 2002.
Aghil et al., "Synthesis and Cytotoxicity of Shikimate Analogues. Structure: Activity Studies Based on 1-Crotonyloxymethyl-3R, 4R, 5R-trihydroxycyclohex-2-enone," Anti-Cancer Drug Design, pp. 67-82 (1992).
Chimura et al., "The Structure of a Glyoxalase I Inhibitor and Its Chemical Reactivity with SH-Compounds," The Journal of Antibiotics, pp. 743-748 (1975).
Hamilton et al., "Glutathionyl Transferase Catalyzed Addition of Glutathione to COMC: A New Hypothesis for Antitumor Activity."
Huntley et al., "A New Synthesis of the Glyoxalase-I Inhibitor COTC," Tetrahedron Letters, pp. 2031-2034 (2000).
Huntley et al., "Reaction of COTC with Glutathione: Structure of the Putative Glyoxalase I Inhibitor," Organic Letters, pp. 3143-3144 (2000).
Jones et al., "Target Directed Enediyne Prodrugs: Cytotoxic Estrogen Conjugates," Tetrahedron Letters, pp. 3643-3646 (1996).
Kavarana et al., "Mechanism-Based Competitive Inhibitors of Glyoxalase I: Intracellular Deliver, in Vitro Antitumor Activities, and Stabilities in Human Serum and Mouse Serum," J. Med. Chem., pp. 221-228 (1999).
Kuduk et al., "Synthesis and Evaluation of Geldanamycin-Testosterone Hybrids," Bioorganic & Medicinal Chemistry Letters, pp. 1303-1306 (2000).
Kuduk et al., "Synthesis and Evaluation of Geldanamycin-Estradiol Hybrids," Bioorganic & Medicinal Chemistry Letters, pp. 1233-1238 (1999).
Lu et al., "Design of Novel Bioconjugates for Targeted Drug Delivery," Journal of Controlled Release, pp. 165-173 (2002).
Maeda et al., "Conjugates of Anticancer Agents and Polymers: Advantages of Macromolecular Therapeutics in Vivo," Bioconjugate Chemistry, pp. 353-362 (1992).
Mirza et al., "Synthesis of a Glyoxalase I Inhibitor from *Streptomyces griseosporeus*. .," Helvetica Chimica Acta, pp. 988-996 (1985).
Rezgui et al., "DMAP-Catalyzed Hydroxymethylation of 2-Cyclohexenones in Aqueous Medium Through Baylis-Hillman Reaction," Tetrahedron Letters, pp. 5965-5966 (1998).
Takeuchi et al., "A Glyoxalase I Inhibitor of a New Structural Type Produced by *Streptomyces*," The Journal of Antibiotics, pp. 737-742 (1975).
Tamura et al., "Asymmetric Synthesis of 3-Substituted 2-exo-Methylenealkanones by Addition-Elimination Reaction Using a Chiral Leaving Group and Organometallic Nucleophiles," J. Org. Chem., pp. 4895-4903 (1992).
Tamura et al., "Stereoselective Synthesis of Cis 2,3-Disu stituted Cycloheptanones by Kinetic Protonation," American Chemical Society, p. 4903 (1992).

* cited by examiner

*Primary Examiner*—Sabiha N. Qazi
(74) *Attorney, Agent, or Firm*—Burns & Levinson, LLP; Jacob N. Erlich, Esq.; Janine M. Susan

(57) ABSTRACT

Described herein are new enone derivatives and conjugates. Additionally, methods for synthesizing these new enones are also disclosed. These compounds can be employed in cancer therapy.

9 Claims, 5 Drawing Sheets

ENONE CANCER THERAPEUTICS

RELATED APPLICATIONS

This continuation application claims priority to and the benefit of U.S. patent application Ser. No. 10/098,834, filed Mar. 15, 2002.

STATEMENT OF GOVERNMENT INTEREST

This work was supported by the National Institutes of Health under grant GM 24054 and by the U.S. Army Medical Research and Material Command under grant DAMD17-99-1-9275. The United States government has certain rights in the invention.

FIELD OF THE INVENTION

This invention relates to novel enones that can be used in enone-containing prodrugs for use as cancer therapeutics. It also relates to methods for synthesizing these novel enones and enone-containing prodrugs.

BACKGROUND OF THE INVENTION

The search for improved chemotherapeutic agents with novel mechanisms of action is driven by several, important, unmet clinical needs. First and foremost, almost all anticancer drugs cause extreme secondary side effects. Moreover, solid tumors, which are subject to abnormally high interstitial pressure, tend to be resistant to drug penetration by simple diffusion. Since diffusion rates correlate closely with molecular weights, the utility of anticancer strategies that rely on high molecular weight species such as monoclonal antibodies, tumor necrosis factor, interleukins, interferons, and other macromolecules for tumor therapy may ultimately be limited. For that reason, the development of new chemotherapeutic agents and strategies based on small molecules that can be targeted selectively to diseased tissues continues to be an important undertaking. Research over the past several decades indicates that some of the best new lead compounds for cancer chemotherapy have emerged from a better understanding of natural compounds possessing antitumor or anticancer activity.

In 1975, the fungal metabolite 2-crotonyloxymethyl-(4R,5R,6R)-4,5,6-trihydroxy-2-cyclohexenone (COTC, 1a, Scheme 1) was found to display potent antitumor activity in vitro (Takeuchi, T.; Chimura, H.; Hamada, M.; Umezawa, H.; Yoshka, H.; Oguchi, N.; Takahashi, Y.; Matsuda, A. A Glyoxalase I Inhibitor of a New Structural Type Produced by *Streptomyces*. *J. Antibiot.* 1975, 28, 737-742). Besides that antitumor activity, it was noted that COTC reacted with reduced glutathione (GSH) to form a new product that inhibited glyoxalase I, a key enzyme in the detoxification of methylglyoxal. In 1975, Chimura et al. attributed the antitumor activity of 1a to its putative glutathione (GSH) adduct 2a, which was proposed to inhibit the enzyme glyoxalase I (GlxI) (Chimura, H.; Nakamura, H.; Takita, T.; Takeuchi, T.; Umezawa, M.; Kato, K.; Saito, S.; Tomisawa, T.; Iitaka, Y. The Structure of a Glyoxalase I Inhibitor and Its Chemical Reactivity with SH Compounds. *J. Antibiot.* 1975, 28, 743-748). In the 25 years since those findings were reported, the inhibition of GlxI by 2a has come to be associated with its antitumor activity, although no direct evidence supports such a causal relationship, and the hypothesis has never been tested.

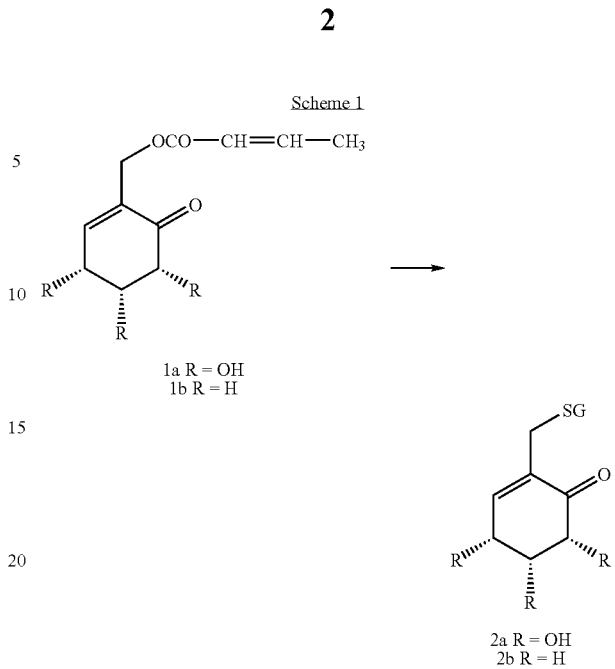

Scheme 1

1a R = OH
1b R = H

2a R = OH
2b R = H

Recently, it has been observed that the simpler COTC analog 1b (COMC) also displayed potent antitumor activity against a range of different murine and human tumors in culture, with 1b being somewhat more potent ($IC_{50}$=0.5-19 µM) than 1a ($IC_{50}$=3-44 µM) (Aghil, O.; Bibby, M. C.; Carrington, S. J.; Doubic, J.; Douglas, K. T.; Phillips, R. M.; Shing, T. K. M. Synthesis and Cytotoxicity of Shikimate Analogues. Structure: Activity Studies Based on 2-Crotonyloxymethyl-3R,4R,5R-trihydroxycyclohex-2-enone. *Anti-Cancer Drug Design* 1992, 7, 67-82). The endocyclic enone function in these compounds was required for antitumor activity. The antitumor activities of 1b were also thought to result from inhibition of GlxI by the corresponding GSH adduct 2b. Neither structure 2a nor 2b had been isolated or characterized, and the structures proposed for 2a and 2b were assigned indirectly, on the basis of model experiments with simple thiols.

GlxI plays a pivotal role in detoxifying intracellular methylglyoxal, which is formed during normal carbohydrate metabolism (Vander Jagt, D. L. The Glyoxalase System. In *Coenzymes and Cofactors: Glutathione*; Dolphin, D.; Poulson, R.; Avramovic, O., Eds.; John Wiley and Sons: New York, 1989; Vol. 3 (part A), pp 597-641.; Creighton, D. J. and Pourmotabbed, T. in *Molecular Structure and Energetics: Principles of Enzyme Activity*, Liebman, J. F. and Greenberg, A., Eds., VCH Publishers, New York 1988, Vol. 9. pp 353-386). Certain inhibitors of human GlxI, the most potent of which are enediol transition state analogue inhibitors, have been shown to retard the growth of both murine and human tumors in culture and in tumor-bearing mice by causing the accumulation of intracellular methylglyoxal (Kavarana, M. J.; Kovaleva, E. G.; Creighton, D. J.; Wollman, M. B.; Eiseman, J. L. *J. Med. Chem.* 1999, 42, 221-228; Sharkey, E. M.; O'Neill, H. B.; Kavarana, M. J.; Wang, H.; Creighton, D. J.; Sentz, D. L.; Eiseman, J. L. *Cancer Chemother. and Pharmacol.* 2000, 46, 156-166).

While a priori plausible, the hypothesis of Takeuchi et al. for the antitumor action of COTC and COMC has never been tested. Recently, authentic samples of both 2a and 2b were prepared by independent synthesis, and shown to be only modest inhibitors of GlxI (Huntley, C. F.; Hamilton, D. S.;

Creighton, D. J.; Ganem, B. *Org. Lett.* 2000, 2, 3143-3144; Hamilton, D. S.; Ding, Z.; Ganem, B.; Creighton, D. J. Glutathionyl Transferase Catalyzed Addition of Glutathione to COMC: A New Hypothesis for Antitumor Activity. *Org. Lett.* accepted and in press) (FIG. 1).

SUMMARY OF THE INVENTION

The endocyclic enone, COMC, is a substrate for glutathionyl transferase, an enzyme that is widely distributed in mammalian tissue. This enzyme catalyzes the addition of glutathione to COMC, forming a reactive intermediate that can, in turn, react with, and covalently modify, functionality on proteins and DNA that may be critical to cell viability. An efficient synthesis of COMC has been developed that is superior to the earlier reported seven-step procedure. The embodiments of this invention include several new families of endocyclic enones which can be conjugated to various moieties, including sex hormone steroid derivatives, that target cancer cells, thus making these conjugates effective anticancer prodrugs. These new endocyclic enones can also be bound to water-soluble copolymers to modify drug solubility and pharmacokinetics during their delivery to treat cancer.

Other objects, features, and advantages of the present invention will be apparent from the following Detailed Description of the Embodiments taken in conjunction with the accompanying drawings in which:

DETAILED DESCRIPTION OF THE INVENTION

Figure 1:
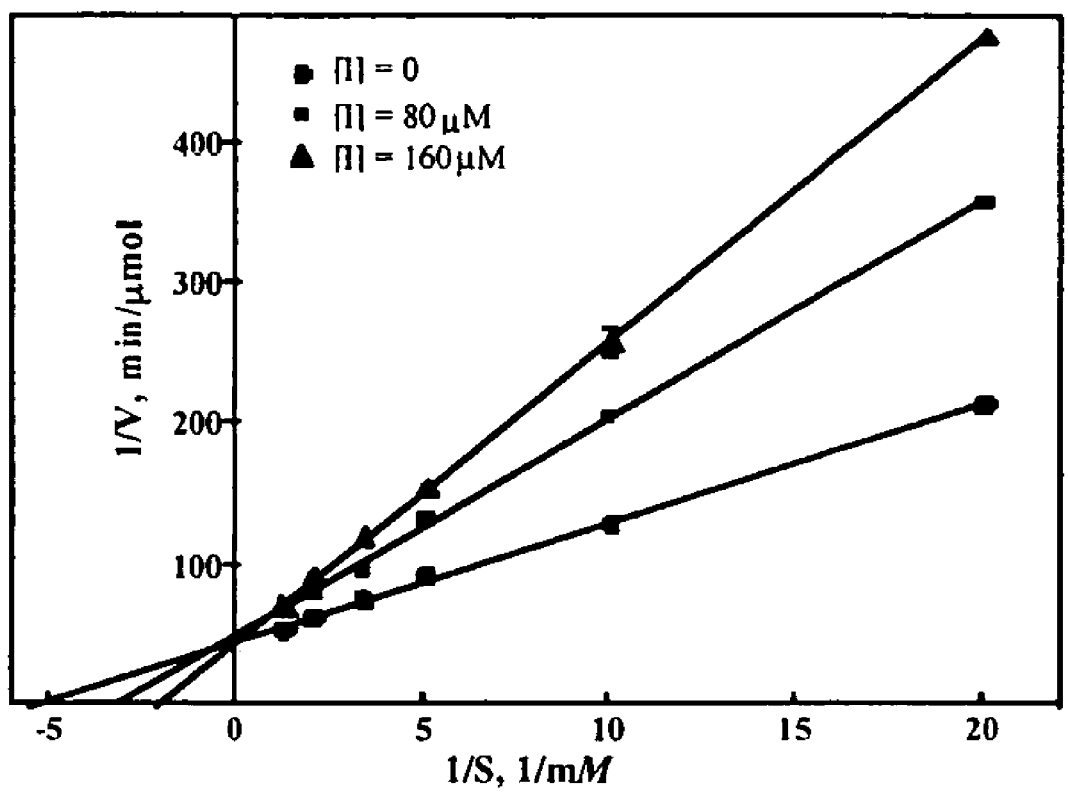
FIG. 1 shows the reciprocal plot of the velocity of the glyoxalase I reaction ($\Delta OD_{240}$) versus the concentration of GSH-methylglyoxal-thiohemiacetal (S) in the absence and presence of different concentrations of 2b. In each kinetic run, the concentration of free GSH was maintained at 0.2 mM by varying the total concentration of GSH and methylglyoxal on the basis of the dissociation constant of the hemithioacetal ($K_{diss}$=2.2 mM). Conditions: 50 mM phosphate buffer, pH 7.0, 25° C.

In order to establish an alternative mode of tumor toxicity for COTC and COMC, we have now demonstrated that COMC is a substrate for glutathionyl transferase, an enzyme that is widely distributed in mammalian tissue. Glutathionyl transferase catalyzes a conjugate addition of GSH to 1b with concomitant elimination of crotonic acid leading to 3-glutathionyl-2-exomethylenecyclohexanone 3 (Scheme 2), a reactive intermediate that has now been isolated and characterized for the first time. Trapping studies with amino acids and nucleotides support the hypothesis that 3 can react with, and covalently modify, functionality on proteins and DNA that may be critical to cell viability.

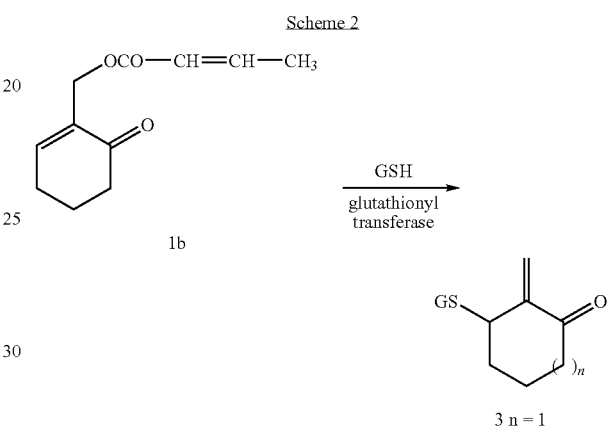

In the course of this work, a short and efficient synthesis of 1b was developed that is superior to the earlier reported seven-step procedure (Hamilton, D. S.; Ding, Z.; Ganem, B.; Creighton, D. J.; *Org. Lett.* accepted and in press). The improved synthesis is depicted in Scheme 3. Baylis-Hillman reaction of 2-cyclohexenone 4 with formaldehyde afforded 2-hydroxymethyl-2-cyclohexenone 5, (Rezgui, F.; El Gaied, M. M. DMAP-Catalyzed Hydroxymethylation of 2-Cyclohexenones in Aqueous Medium Through Baylis Hillman Reaction. *Tetrahedron Lett.* 1998, 39, 5965-5966) which was then crotonylated to 1b following the literature procedure. (Mirza, S.; Molleyres, L. -P.; Vasella, A. Synthesis of a Glyoxalase I Inhibitor from *Streptomyces griseosporeus* Niida et Ogasawara. *Helv. Chim. Acta* 1985, 68, 988-996).

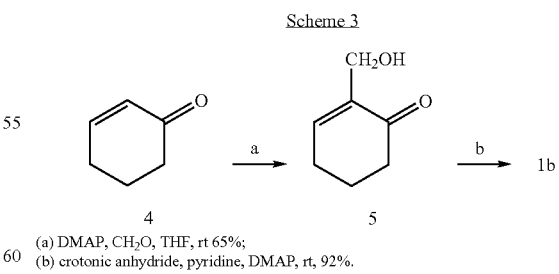

(a) DMAP, $CH_2O$, THF, rt 65%;
(b) crotonic anhydride, pyridine, DMAP, rt, 92%.

The GSH conjugate 2b was prepared from 1b by adapting the procedure for making 2a from 1a (Huntley, C. F. M.; Wood, H. B.; Ganem, B. A New Synthesis of the Glyoxalase-I Inhibitor COTC. *Tetrahedron Lett.* 2000, 41, 2031-2034). The NMR spectrum of 2b featured the expected glutathionyl resonances and the downfield resonance (δ7.12, triplet) characteristic of H3 in β, gamma-unsubstituted 2-cyclohexenones.

Figure 2:
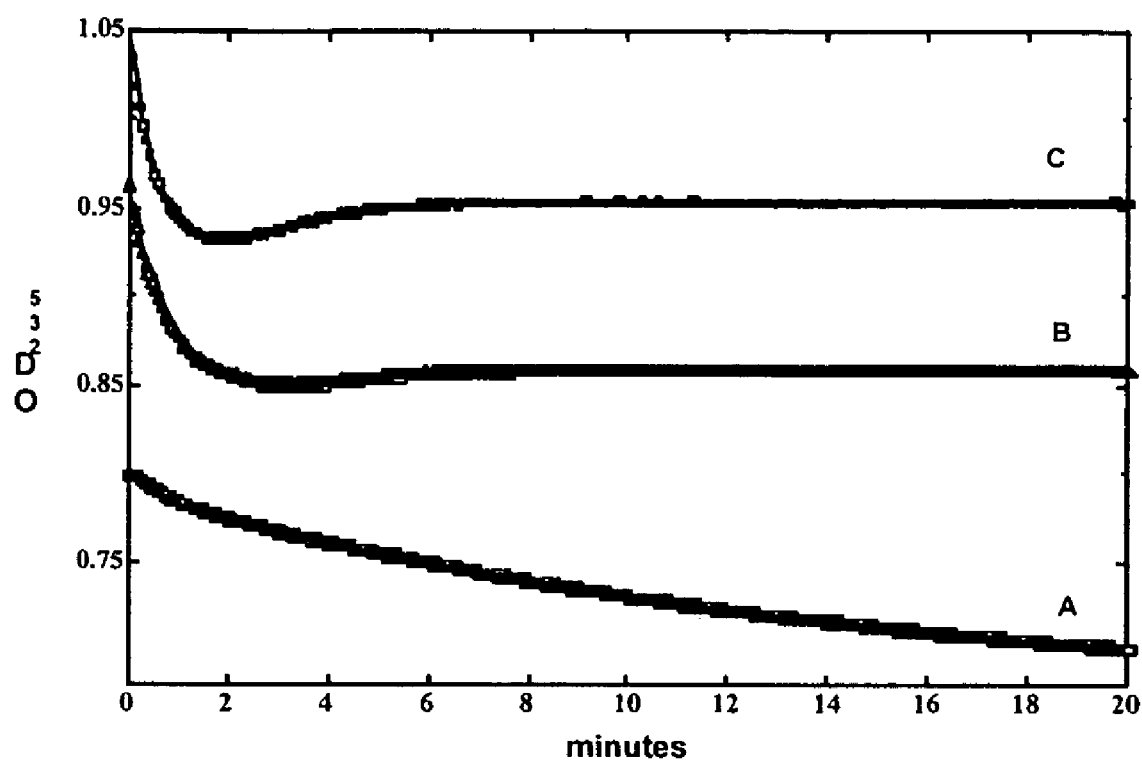
FIG. 2 shows the spectrophotometrically determined rates of reaction of GSH (1.03 mM) with 1b (0.05 mM) (A) in the absence GST (k=0.070±0.0002 min$^{-1}$), (B) in the presence 1.8 units of GSTP1-1 ($k_1$=0.882±0.055 min$^{-1}$; $k_2$=0.633±0.053 min$^{-1}$), and (C) in the presence of 2.4 units of GSTP1-1 ($k_1$=1.33±0.037 min$^{-1}$; $k_2$×0.685±0.024 min$^{-1}$).

Kinetic studies with human erythrocyte GlxI (sodium phosphate buffer, pH 7.0, 25° C., FIG. 1) indicated that 2b was a competitive inhibitor of the enzyme, with a dissociation constant $K_i = 107 \pm 0.1$ μM. It has previously been reported that 2a competitively inhibited human erythrocyte GlxI, with a dissociation constant $K_i = 183 \pm 6$ μM (Huntley, C. F. M.; Wood, H. B.; Ganem, B. A New Synthesis of the Glyoxalase-I Inhibitor COTC. *Tetrahedron Lett.* 2000, 41, 2031-2034). To investigate the mechanism of formation of 2b, the nonenzymatic reaction of 1b with GSH was monitored spectrophotometrically, and followed a simple first-order decay (FIG. 2, trace A). No intermediate species was detectable. However, in the presence of human placental glutathione transferase (GSTP 1-1) (Predominantly the pi or P1-1 isoform, purchased from Sigma Chemical Company. Salts and free GSH were removed by ultrafiltration. Units of transferase activity were determined using 1-chloro-2,4-dinitrobenzene as substrate (Mannervik, B.; Danielson, U. H. *CRC Critical Reviews in Biochemistry* 1988, 23, 283-337). The reaction rate profile conformed to a double exponential decay, composed of a rapid, enzyme-dependent, initial phase involving 1b followed by a slower enzyme-independent first-order phase (FIG. 2, traces B and C).

This finding was consistent with the mechanism shown in Scheme 4, whereby an initial, enzyme-catalyzed Michael addition of GSH to 1b afforded the exocyclic enone 3. Once dissociated from the enzyme, free 3 reacted with GSH nonenzymatically to form 2b.

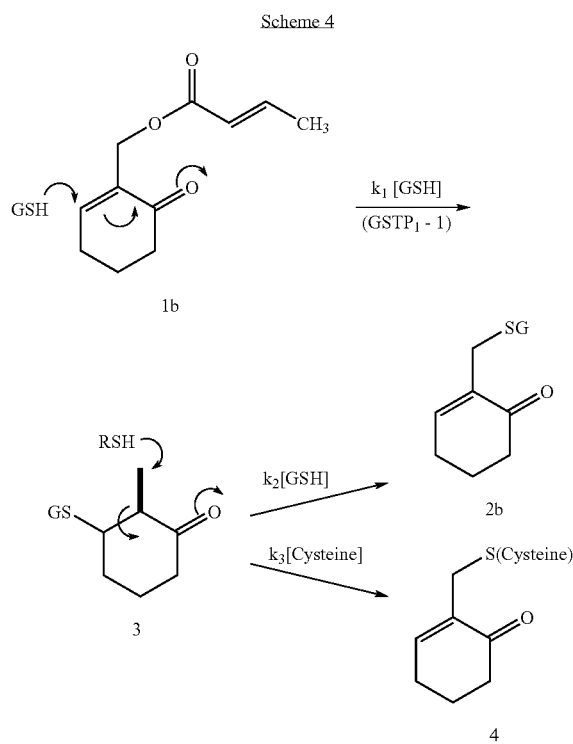

Scheme 4

Figure 3:
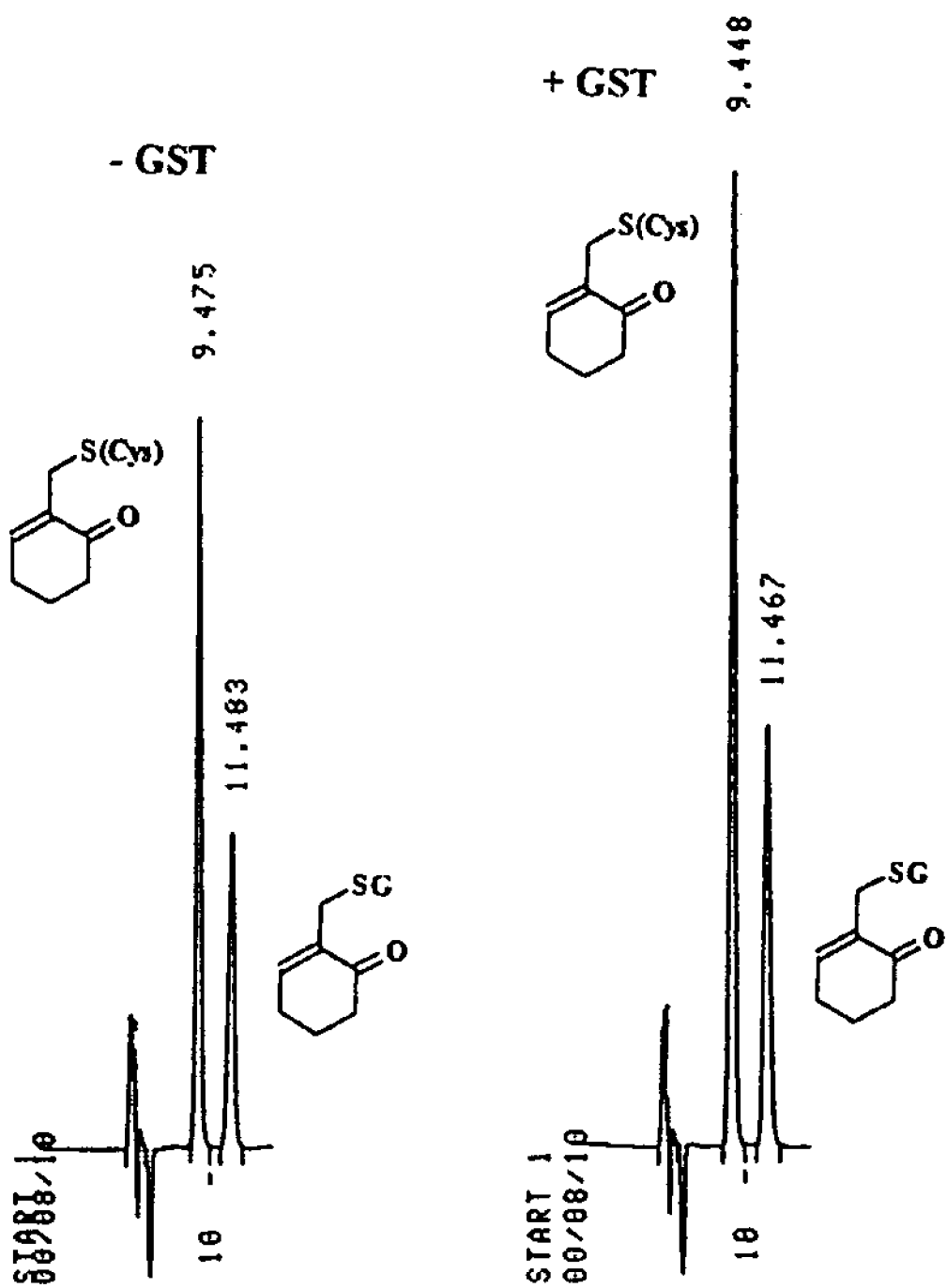
FIG. 3 shows the fractionation of product mixtures in the absence and presence of GSTP1-by reverse phase HPLC (Waters, μ-Bondapak $C_{18}$, 0.78×30 cm ) after 30 min incubation of reaction mixtures initially composed of 1b (0.1 mM), cysteine (0.5 mM), GSH (0.5 mM), 0.1 M $KP_i$ (pH 6.5) and EDTA (0.05 mM) at 25° C. Based on the integrated intensities of the well-resolved peaks corresponding to 4 (~9.5 min) and 2b (~11.5 min), the product ratio in the presence of GSTP 1-1 was identical to that obtained from a nonenzymatic incubation of 1b with the same concentrations of cysteine and GSH (FIG. 3). That finding indicated that 3 dissociated from the enzyme prior to reacting with the free thiols in solution, and was consistent with the mechanism in Scheme 4. Adduct 2b (0.5 mM) was stable under the reaction conditions, undergoing less than 1% conversion to 4 in the presence of cysteine (2.5 mM) over 27 h, as determined by HPLC.

When 1b (0.1 mM) was incubated with cysteine (0.5 mM) and GSH (0.5 mM) in the presence of $GSTP_1$-1 (1.5 units) for 30 min and the reaction mixture fractionated by reverse phase HPLC, thiol adducts 2b and 4 were isolated. Based on the integrated intensities of the well-resolved peaks corresponding to 4 (~9.5 min) and 2b (~1.5 min), the product ratio in the presence of GSTP1-1 was identical to that obtained from a nonenzymatic incubation of 1b with the same concentrations of cysteine and GSH (FIG. 3). That finding indicated that 3 dissociated from the enzyme prior to reacting with the free thiols in solution, and was consistent with the mechanism in Scheme 4. Adduct 2b (0.5 mM) was stable under the reaction conditions, undergoing less than 1% conversion to 4 in the presence of cysteine (2.5 mM) over 27 h, as determined by HPLC.

Initial rates of reaction of 1a and 1b with hGSTP1-1 were determined from reciprocal plots of initial velocities ($\Delta OD_{235}$/min), versus [substrate] in buffered solution at pH 6.5, with [GSH]=1 mM (25° C.). Under those conditions, the enzyme-catalyzed GSH addition became rate determining (<0.01 units of transferase in the assay cuvettes). For 1b, $k_{cat} = 1.2 \pm 0.2$ s$^{-1}$ and $K_m = 52 \pm 10$ μM. For 1a, the individual kinetic constants could not be accurately determined, although $k_{cat}/K_m$ was estimated to be 8.3-fold lower than that of 1b.

Figure 4:
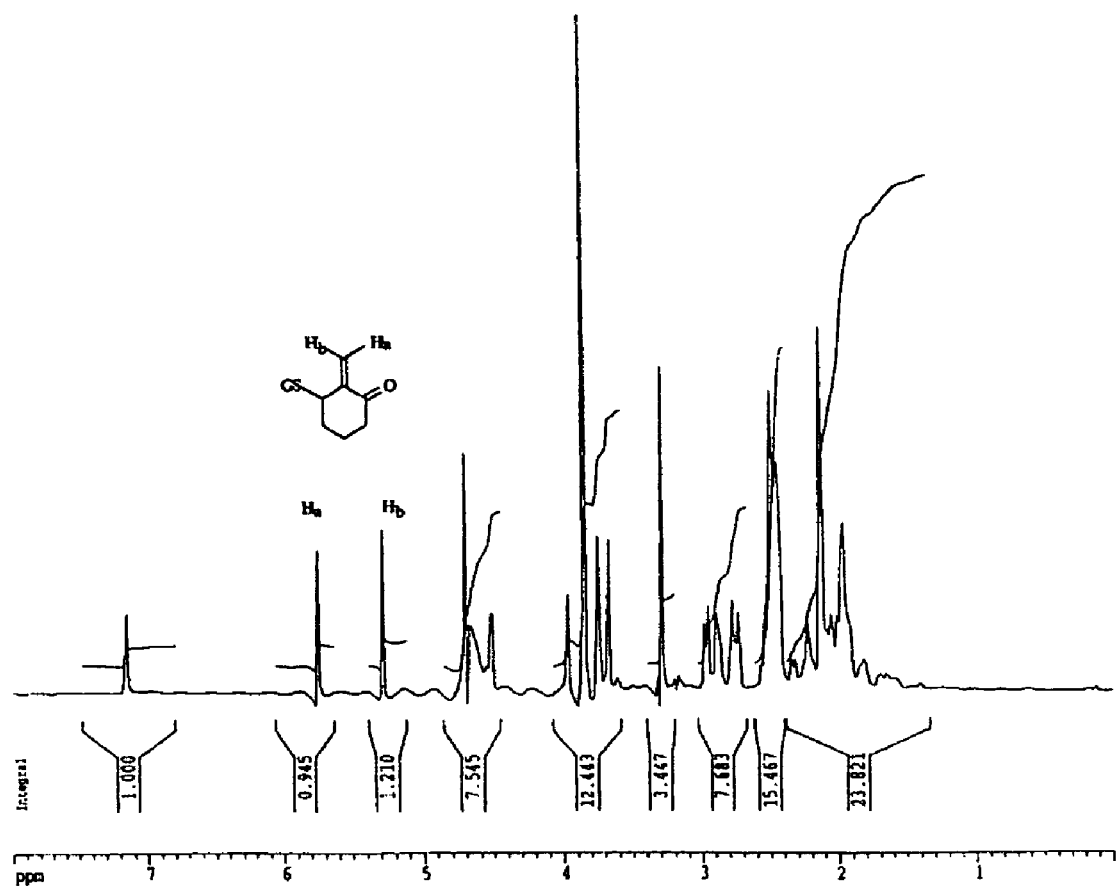
FIG. 4 shows the 600 MHz $^1$NMR spectrum of the putative exocyclic enone 3. The resonance at 7.16 ppm is due to contaminating adduct 2b. The other resonances in the spectrum are those expected for S-substituted GSH derivatives.

Brief incubation of a mixture of 1b, GSH, and GSTP 1-1 gave rise to a transient intermediate that could be isolated by reverse-phase HPLC, with a retention time close to that of synthetic 2b. The 600 MHz $^1$NMR spectrum of the intermediate was consistent with the structure of 3 (FIG. 4). The vinyl proton resonances at 5.76 and 5.29 ppm were characteristic of geminal vinylic hydrogens, and consistent with published NMR spectra of several closely related 2-methylenecyclohexanones (Tamura, R.; Watabe, K.; Ono, N.; Yamamoto, Y. *J. Org. Chem.* 1992, 57, 4895-4903.) Other resonances in the spectrum corresponded to those expected for the tripeptide moiety (Rabenstein, D. L.; Keire, D. A. in *Coenzymes and Cofactors: Glutathione*; Dolphin, D.; Poulson, R.; Avramovic, O., Eds.; John Wiley, New York, 1989; Vol 3, Part A, pp. 67-101). The resonance at δ7.12 indicated the presence of 2b, which was formed in the transferase-independent addition of GSH to 3.

Thus, comparative data analysis suggested that the potent antitumor activities of COTC (1a) and COMC (1b) cannot be rationalized by the action of 2a and 2b, respectively, as weak competitive inhibitors of human erythrocyte GlxI. Earlier reported enediol analogue inhibitors of GlxI that inhibited the growth of L1210 and B16 melanotic melanoma in vitro in ester prodrug form exhibited $K_i$ values in the submicromolar range (Kavarana, M. J.; Kovaleva, E. G.; Creighton, D. J.; Wollman, M. B.; Eiseman, J. L. Mechanism-Based Competitive Inhibitors of Glyoxalase I: Intracellular Delivery, In Vitro Antitumor Activities, and Stabilities in Human Serum and Mouse Serum. *J. Med. Chem.* 1999, 42, 221-228). The $IC_{50}$ values of the prodrugs were approximately proportional to the $K_i$ values of the enzyme inhibitors, such that the weakest enzyme inhibitor ($K_i$=0.16 μM) gave an $IC_{50}$ value>100 μM. On this basis, 2b should exhibit very poor antitumor potency, in contrast with the observed antitumor activity of 1b ($IC_{50}$=0.5-19 μM) (Aghil, O.; Bibby, M. C.; Carrington, S. J.; Double, J.; Douglas, K. T.; Phillips, R. M.; Shing, T. K. M. *Anti-Cancer Drug Design* 1992, 7, 67-82).

Figure 5:
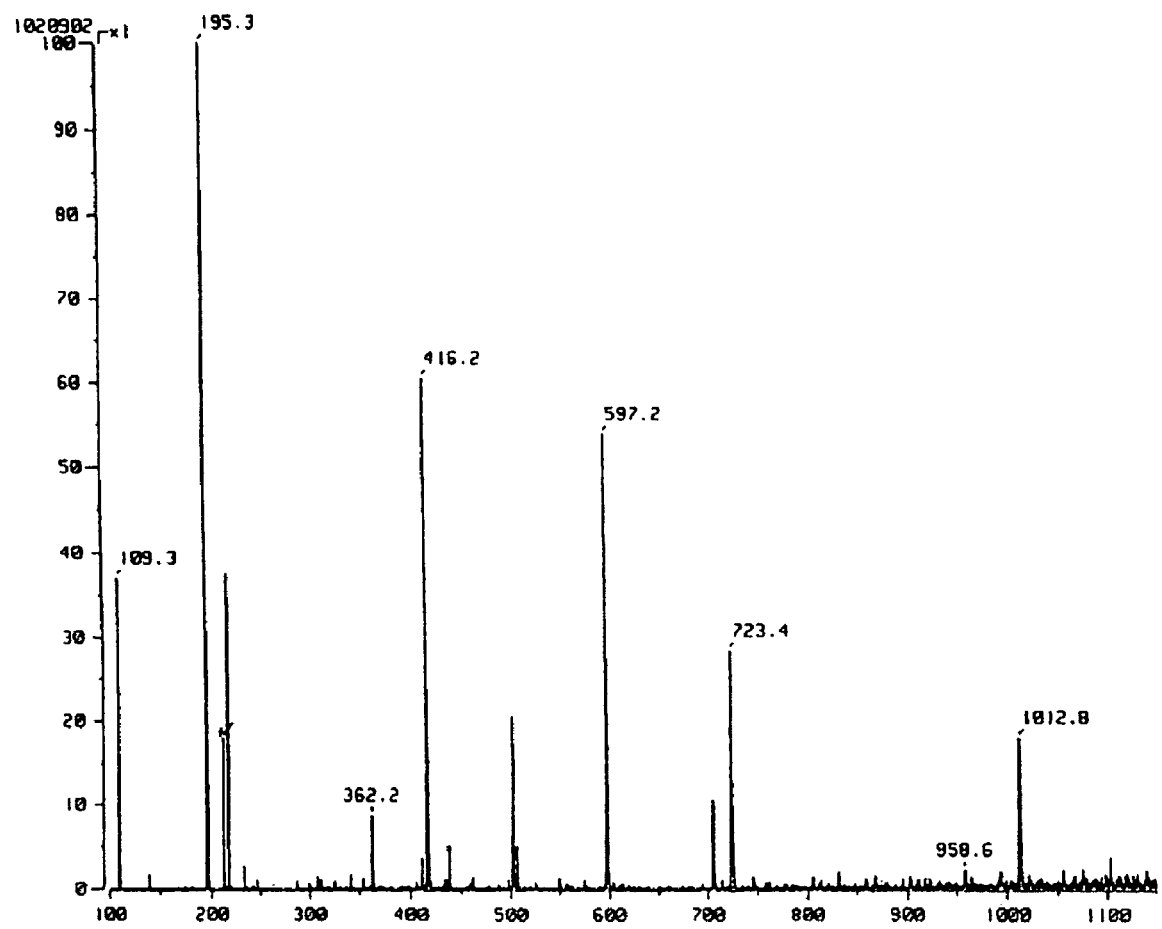
FIG. 5 shows the MALDI spectrum of a two hour incubation mixture composed of ApA, GSH (0.5 mM), 1b (0.1 mM) and GST (0.5 units), phosphate buffer (50 mM, pH 7), 25° C.

In principle, cytotoxicity could result from alkylation of DNA and/or proteins critical to cell function. Using COMC to test this hypothesis, the dinucleotides ApA, GpA and CpC were separately incubated with 0.5 mM GSH, 0.1 mM 1b and 0.5 units GSTP1-1. After two hours, the incubation mixtures were analyzed by matrix assisted laser desorption mass spectrometry (MALDI, FIG. 5). In all cases, significant concentrations of nucleotide adducts as well as GSH adducts were detected.

As indicated above, an alternative biological mechanism has now been established for the tumoricidal activity of both COTC and COMC. It may now be hypothesized that 1a and 1b are enzyme-activated prodrugs in which the crotonate ester serves as a leaving group, in a process triggered by glutathionyl transferase.

The embodiments of the invention, shown in Scheme 5, include several new families of endocyclic enones 1, 6, 7, 8, 9, and 10 wherein X is a nucleophilic atom selected from the group consisting of S, N, and O; R is selected from the group consisting of COCH=CHCH$_3$, COCH$_3$, COC$_6$H$_5$, OCON-HCH$_3$ which are antitumor prodrugs, and substrates for the enzyme glutathionyl transferase, an enzyme that is widely distributed in mammalian tissue. The embodiments also include the derived glutathione adducts 3, 6b, 7b, 8b, 9b, and 10b, which are previously unknown compositions of matter, and which can be prepared, inter alia, using glutathionyl transferase.

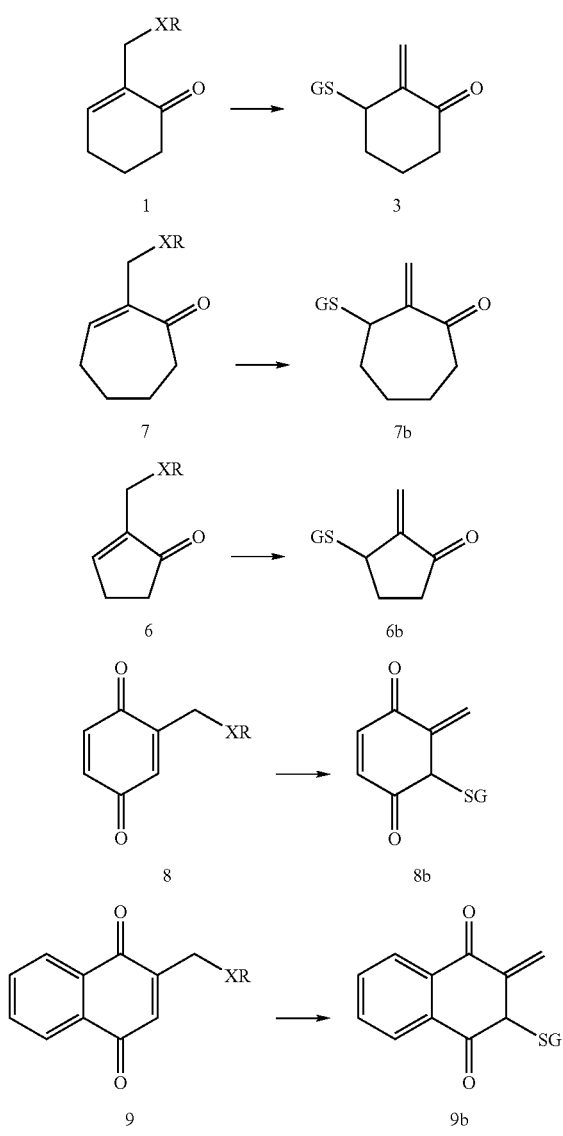

Scheme 5

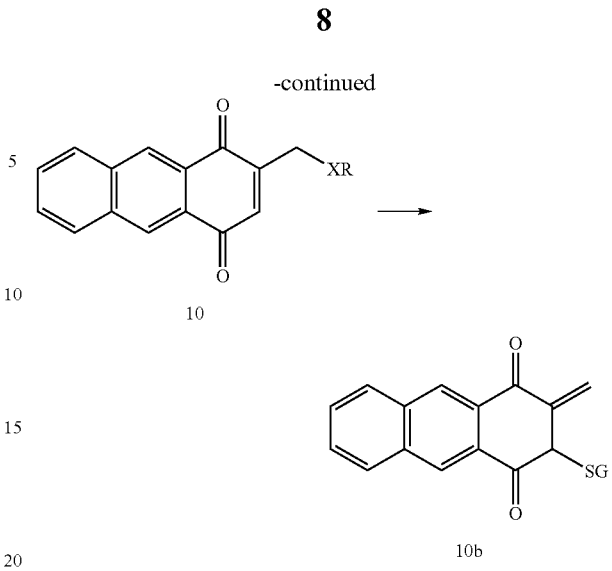

A key novel feature of the invention is the opportunity to take advantage of the prodrug properties of COMC to selectively target certain tumor tissues. Embodiments of the invention that demonstrate this feature include several COMC analogs that use hormones to direct cytotoxic agents to targeted tissues. For example, Kuduk et al. covalently linked geldanamycin (GDM) to testosterone, and demonstrated that the resulting conjugates selectively inhibited prostate cancer cells containing the androgen receptor (Kuduk, S. D., Harris, C., Zheng, F. F., Sepp-Lorenzino, L., Ouerfelli, Q., Rosen, N., and Danishefsky, S. J. "Synthesis and Evaluation of Geldanamycin-Testosterone Hybrids," *Bioorg. Med. Chem. Lett.* 2000, 10, 1303-1306). GDM exerts its toxic effects by binding to the Hsp9O chaperone protein resulting in the degradation of several key signaling proteins. By analogy, testosterone conjugates built on frameworks 1 and 6-10 would also be expected to exhibit selective toxicity towards prostate tumors.

Kuduk et al. also synthesized conjugates of GDM with estradiol and reported that the hybrid compounds were more selective and active than GDM in causing degradation of the estrogen receptor and HER2, a transmembrane kinase linked to a significant number of breast cancers (Kuduk, S. D., Zheng, F. F., Sepp-Lorenzino, L., Rosen, N., and Danishefsky, S. J. "Synthesis and Evaluation of Geldanamycin-Estradiol Hybrids," *Bioorg. Med. Chem. Lett.* 1999, 9, 1233-1238). In related work, conjugates of enediyne antitumor agents with diethylstilbestrol, a powerfil agonist of the estrogen receptor, have been prepared by Jones et al. (Jones, Graham B.; Huber, Robert S.; Matthews, Jude E.; Li, A. "Target Directed Enediyne Prodrugs: Cytotoxic Estrogen Conjugates," *Tetrahedron Lett.* 1996, 37, 3643-3646). These conjugates causes DNA strand scission at $10^{-3}$ M, and are cytotoxic against the MCF-7 human breast cancer cell line.

Embodiments of the present invention include agent 11, which hybridizes COMC with diethylstilbestrol, a powerful estrogen receptor agonist. Compounds 12-14 are estradiol conjugates that also target against breast cancer. The embodiments also include the derived glutathione adducts of these female sex hormone conjugates, which are previously unknown compositions of matter, and which can be prepared, inter alia, using glutathionyl transferase.

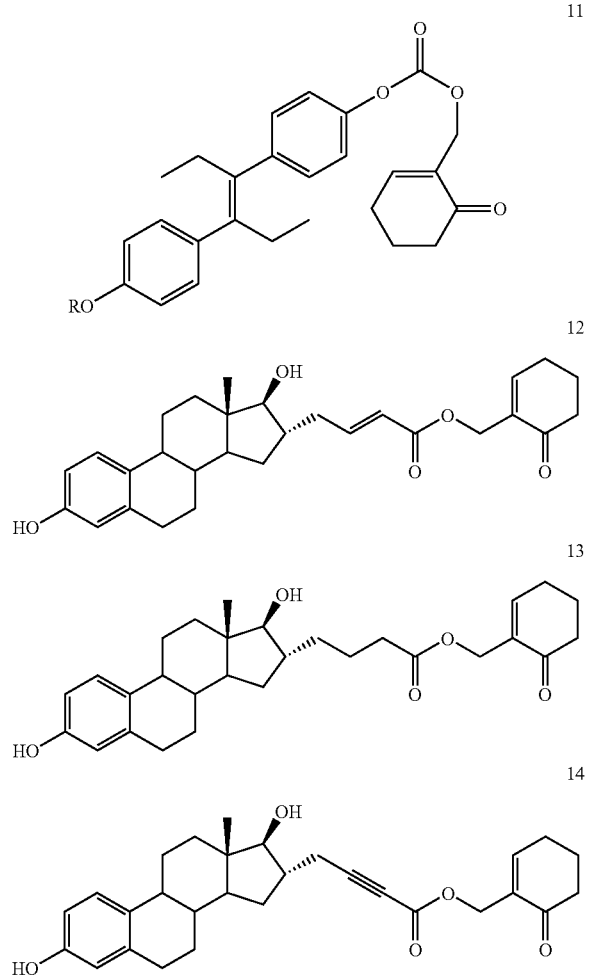

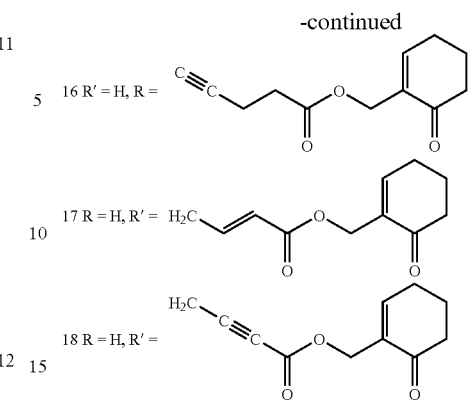

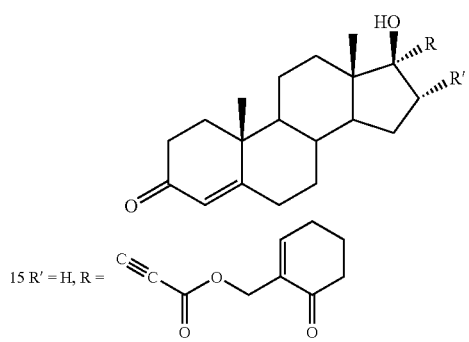

Another set of embodiments of the invention includes the testosterone-linked conjugates 15-18. These embodiments were based on work of Kuduk et al. indicating that the C17-β-hydroxyl group of testosterone is required for strong binding to the androgen receptor. Furthermore, conjugates based on C17 α-linked alkyne tethers displayed the most potent activities. The embodiments also include the derived glutathione adducts of these testosterone conjugates, which are previously unknown compositions of matter, and which can be prepared, inter alia, using glutathionyl transferase.

Another embodiment of the invention comprises polymeric substances in which COMC molecules are bound to water-soluble N-(2-hydroxypropyl) methacrylamide (HPMA) copolymers. Such HPMA copolymers have been used as drug carriers to modify the solubility and pharmacokinetics of the drug (Lu, Z. -R.; Shiah, J. -G.; Sakuma, S.; Kopeckova, P.; Kopecek, J. *Journal of Controlled Release* 2002, 78, 165-173). The derived copolymer-drug conjugates have been shown to accumulate efficiently in tumor tissue because of the tumor's leaky vasculature and enhanced permeability. That effect, known as the enhanced permeability and retention (EPR) effect (Maeda, H.; Seymour, L. M.; Miyamoto, Y. *Bioconjugate Chem.* 1992, 3, 351-362.), makes possible the efficient treatment of solid tumors, provided the surrounding tumor tissue contains enzymes that can release the active antitumor agent from the polymer.

The conjugate of COMC with the HPMA copolymer shown in structure 19 is subject to the EPR effect, and can release active antitumor agent 3 from the polymer by the action of glutathionyl transferase, which is widely distributed throughout mammalian tissue types.

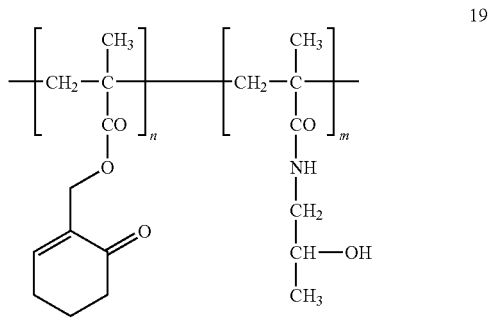

These new cancer therapeutics will be manufactured as standard physiologically acceptable salts and derivatives formulated with the appropriate pharmaceutical materials. The enones developed can be delivered either alone or in combination with other cancer therapeutics that may enhance their pharmaceutical effects. Methods for delivering the enones and any additional cancer therapeutics combined with it will likely be either oral or intravenous, but other methods of delivery are also possible. The components of any combination can be delivered by the same or separate methods and they can be administered simultaneously or separately in time.

The present invention is illustrated by the previous examples. However, it should be understood that the invention is not limited to the specific details of these examples. It will now be apparent to those skilled in the art that other embodiments, improvements, details, and uses can be made that are consistent with the letter and spirit of the foregoing disclosure and within the scope of this patent and the appended claims.

What is claimed is:

1. A compound of Formula 7

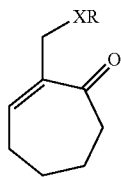

7 wherein X is a nucleophilic atom selected from the group consisting of S, N, and O and R is selected from the group consisting of COCH$_3$, COC$_6$H$_5$ and CONHCH$_3$; stereoisomers and positional isomers thereof.

2. The compound of claim 1, wherein said compound is bound to a water-soluble copolymer.

3. The compound of claim 2, wherein said water-soluble copolymer comprises N-(2-hydroxypropyl)methacrylamide copolymer.

4. A compound of Formula 1 or 6

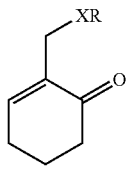

1

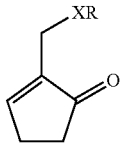

6 wherein X is a nucleophilic atom selected from the group consisting of S and N; and R is selected from the group consisting of COC$_6$H$_5$ and CONHCH$_3$; stereoisomers and positional isomers thereof.

5. The compound of claim 4, wherein said compound is bound to a water-soluble copolymer.

6. The compound of claim 5, wherein said water-soluble copolymer comprises N-(2-hydroxypropyl)methacrylamide copolymer.

7. A compound of Formula 1 or 6

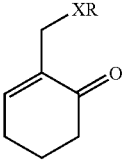

1

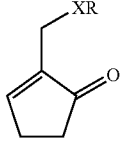

6 wherein X is a nucleophilic atom selected from the group consisting of S, N and O; and R is CONHCH$_3$; stereoisomers and positional isomers thereof.

8. The compound of claim 7, wherein said compound is bound to a water-soluble copolymer.

9. The compound of claim 8, wherein said water-soluble copolymer comprises N-(2-hydroxypropyl)methacrylamide copolymer.

* * * * *